United States Patent
Burch

(10) Patent No.: US 6,206,003 B1
(45) Date of Patent: Mar. 27, 2001

(54) MASK WITH INTEGRAL VALVE

(76) Inventor: John M. Burch, 2512 Horseman, Plano, TX (US) 75025

( * ) Notice: Subject to any disclaimer, the term of this patent is extended or adjusted under 35 U.S.C. 154(b) by 0 days.

(21) Appl. No.: 09/210,035

(22) Filed: Dec. 11, 1998

(51) Int. Cl.[7] ................................................. A62B 18/02
(52) U.S. Cl. ................................ 128/206.21; 128/207.12
(58) Field of Search .................... 128/201.24, 201.28, 128/205.24, 206.21, 206.24, 206.26, 206.28, 207.12, 202.22, 205.23, 206.12, 206.15, 207.11

(56) References Cited

U.S. PATENT DOCUMENTS

| | | | |
|---|---|---|---|
| 4,098,271 | * 7/1978 | Maddock | 128/142.3 |
| 4,245,631 | 1/1981 | Wilkinson et al. | 128/204.17 |
| 4,433,685 | * 2/1984 | Giorgini et al. | 128/204.26 |
| 4,827,964 | * 5/1989 | Guido et al. | 137/81.1 |
| 4,955,374 | 9/1990 | Pasternack | 128/207.12 |
| 5,057,822 | * 10/1991 | Hoffman | 340/611 |
| 5,070,872 | 12/1991 | Neuber | 128/205.24 |
| 5,295,478 | 3/1994 | Baldwin | 128/203.11 |
| 5,438,981 | 8/1995 | Starr et al. | 128/205.24 |
| 5,645,049 | 7/1997 | Foley et al. | 128/203.29 |
| 5,651,361 | * 7/1997 | Dearman et al. | 128/205.25 |
| 5,913,307 | * 6/1999 | Taieb et al. | 128/205.23 |
| 5,944,054 | * 8/1999 | Saieva | 137/625.4 |
| 6,016,802 | * 1/2000 | Jackson | 128/205.25 |

\* cited by examiner

Primary Examiner—John G. Weiss
Assistant Examiner—Teena Mitchell
(74) Attorney, Agent, or Firm—Anderson, Levine & Lintel, LLP

(57) ABSTRACT

A mask for transmitting gases to and from a patient or other user includes a valve which selectively blocks or enables the flow of gases through a port. In one embodiment, the state of the valve is automatically controlled in response to whether the mask is in contact with the patient. In another embodiment, the valve on the mask is manually controlled.

13 Claims, 5 Drawing Sheets

MASK WITH INTEGRAL VALVE

CROSS-REFERENCE TO RELATED APPLICATIONS

Not Applicable

STATEMENT OF FEDERALLY SPONSORED RESEARCH OR DEVELOPMENT

Not Applicable

BACKGROUND OF THE INVENTION

1. Technical Field

This invention relates in general to masks for medical purposes and, more particularly, to a mask for reducing gaseous leakage.

2. Description of the Related Art

Gas delivery masks are used throughout the medical industry for a variety of applications in which a gas is delivered to a patient. One significant application is the administration of anesthesia to a patient. A typical mask for this purpose is shown in FIG. 1.

The mask 10 of FIG. 1 comprises a face plate 12 having an outer seal 14 which interfaces with the patient's face. The mask 10 includes a port 16 through which inhalation gases are conveyed to the patient and exhaled gases are released. A breathing circuit 18 is coupled to the port. The breathing circuit 18 includes a first tube 20 for carrying the inhalation gas and a second tube 22 for carrying the exhalation gas. The first and second tubes 20 and 22 can be connected in a "Y" configuration as shown in FIG. 1, or in a concentric configuration where one of the tubes 20 or 22 is disposed within the other of the tubes 20 or 22.

A problem with any mask of this type, is that the mask 10 may separate from the patient's face. A typical example where the seal is lost between the patient and the mask occurs when the patient is holding the mask to his and her face and then passes out. In this instance, the gases intended for the patient will escape to the area surrounding the patient where they are inadvertently consumed by medical personnel. In the anesthetic field, these gases are often referred to as waste anesthetic gases or WAGs.

Exposure to WAGs can be extremely detrimental to the health of medical care workers. Some of the gases which are considered harmful include nitrous oxide and halogenated gases such as halothane, enflurane, methoxyflurane, trichloroethylene, and chloroform. The affected personnel include nurses, anesthesiologists, surgeons, obstetricians, gynecologist, operating room technicians, dentists and dental personnel, veterinarians and veterinarian personnel.

In the case of nitrous oxide, a pressure activated valve coupled between the gas source and the first tube 20, external to the mask 10, is used to prevent nitrous oxide from being delivered to the first tube 20, except when pressure caused by the patient's inhalation causes the valve to open. This type of pressure activated valve, however, is expensive and, therefore, not used in many cases.

Accordingly, there is a need in the industry to reduce waste anesthesia (or other) gases from entering the environment.

BRIEF SUMMARY OF THE INVENTION

In a first embodiment of the present invention, a mask includes a face plate having a port disposed therein for coupling to a gas source, a seal surrounding said face plate for contacting a patient's face during use of the mask, and a valve coupled between the seal and the port. The valve maintains an open position to allow passage of a gas through port when said seal is in contact with the patient's face and maintains a closed position to restrict flow of said gas through the port when said seal is not in contact with the patient's face.

In a second embodiment of the present invention, a mask includes a shell having a port through which gases may pass. A manually controllable valve can selectively block or enable gas flow through the port.

The present invention provides significant advantages over the prior art. Potentially dangerous gases are blocked at the mask when the mask is not being used by a patient (or other user). Accordingly, the gases cannot escape into the environment proximate the patient, where they can cause significant harm.

BRIEF DESCRIPTION OF THE SEVERAL VIEWS OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

The present invention is best understood in relation to FIGS. 2–7 of the drawings, like numerals being used for like elements of the various drawings.

Figure 2A:
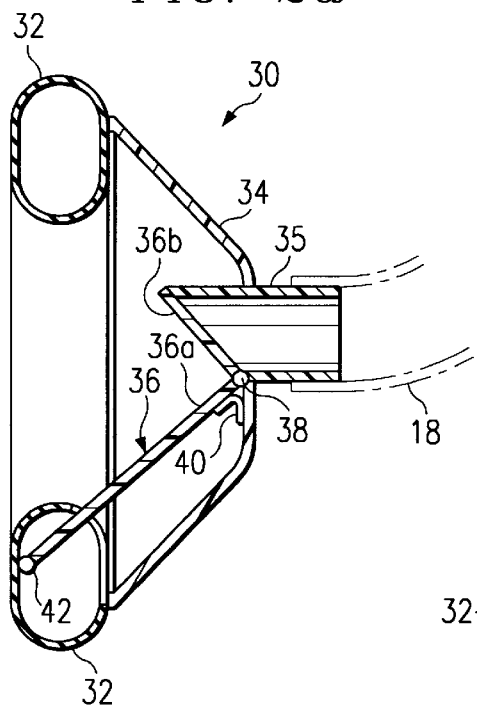
FIGS. 2a, 2b, 2c and 2d illustrate cross sectional side and front views of a first embodiment of a gas delivery mask which controls gas flow through a port responsive to a positive seal between the mask and the patient.
Figure 2B:
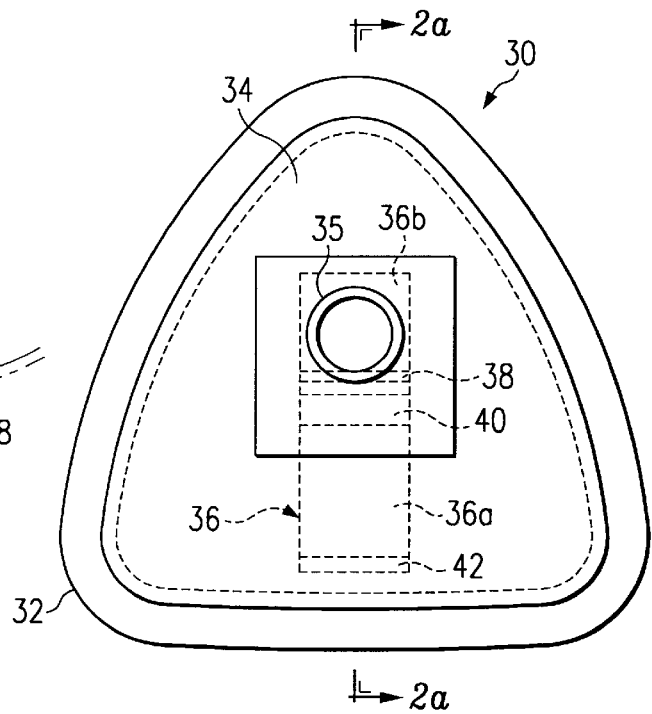
Figure 2C:
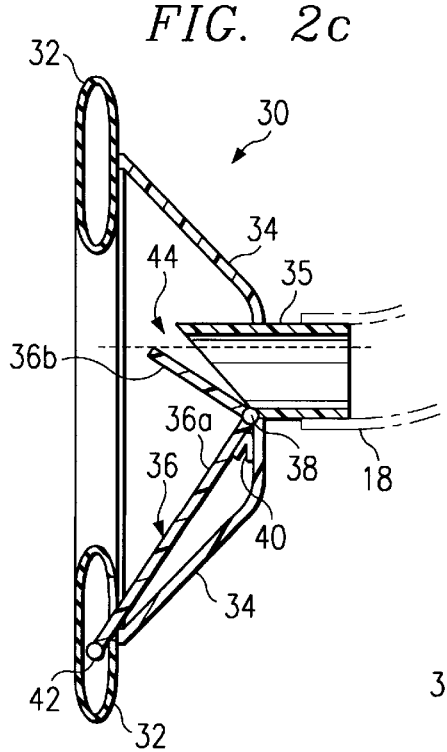
Figure 2D:
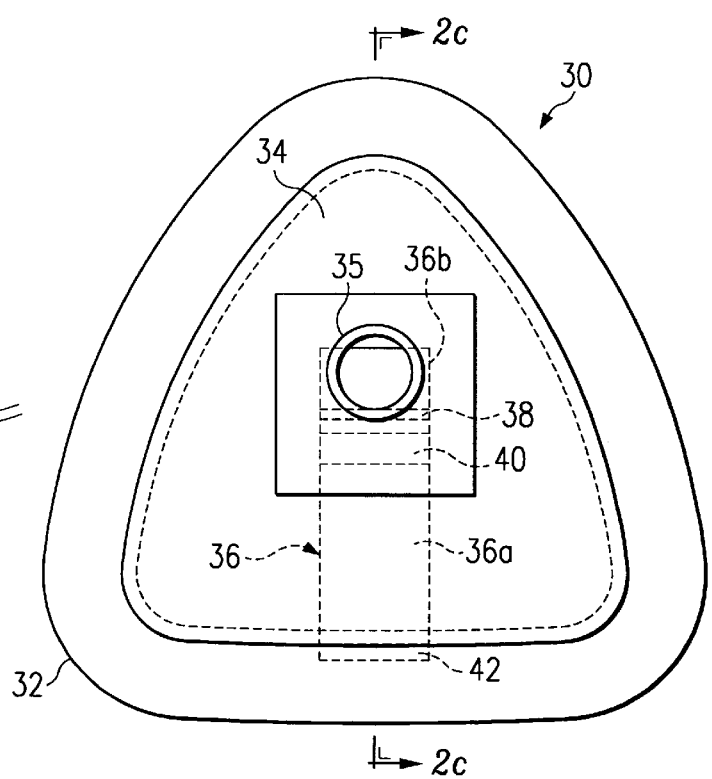

FIGS. 2a through 2d, respectively, illustrate side and front views of a first embodiment of a mask for use in delivering a source gas to a patient which reduces gases from escaping when the mask is not in contact with the patient's face (or in non-medical situations, to the user's face). FIGS. 2a and 2b illustrate side cross-sectional and front views, respectively, of the mask in a state where it is not sealed to the patient's face. FIGS. 2c and 2d illustrate side cross sectional and front views respectively, of the mask in a state where the mask is in contact with the patient's face. The mask 30 includes a seal 32 which surrounds a face plate. Seal 32 may simply be the outer edge of the face plate 34 or it may be formed of a separate piece and coupled to the face plate. The face plate 34 has a port 35 which allows the source gas to pass to the patient (through breathing circuit 18, shown in phantom) and exhaled gases to pass to a gas recovery system. Disposed within the face plate 34 is a valve mechanism 36 which enables or restricts gas flow through the port 35, responsive to whether or not the seal is in contact with the patient's face.

In the embodiment of FIGS. 2a–d, the valve mechanism 36 comprises two segments 36a and 36b, coupled by hinge 38. Valve 36 is maintained in a normally-closed position by spring 40. In the illustrated embodiment, the end of valve segment 36a is disposed within seal 32; alternatively, the end of valve segment 36a could be within face plate 34 where it will contact the patient's face while the mask is worn. Segment 36a may include a rolling mechanism 42 to help it slide along the bottom of seal 32 (or, alternatively, against the patient's face).

In operation, when the mask is not in contact with a patient's face, the seal 32 is in an expanded state, as shown in FIGS. 2a and 2b. The spring 40 rotates valve segments 36a–b such that segment 36b closes the port 35. Accordingly, in this state, any gases in breathing circuit 18 do not pass through port 35 into the atmosphere. In order to maintain port 35 in a closed position, spring 40 should provide sufficient pressure to overcome the pressure of the gas in the breathing circuit 18.

FIGS. 2c and 2d illustrate the mask 20 when it is applied to the face of a patient. In this state, pressure from the patients face compresses the seal 32, forcing segment 36a to rotate against the force of spring 40. As segment 36a rotates, segment 36b, which is held at a fixed angle to segment 36a, rotates away from port 35, resulting in an opening 44 through which gases can pass through port 35. In this state, the patient can breathe gases from the breathing circuit 18 and exhale gases into the breathing circuit 18.

Alternatively, the patient's face could directly contact valve segment 36a such that it is rotated against the force of spring 40. As described above, the contact between the patient's face and the valve 36 would cause the valve 36 to assume an open state, resulting in an opening through which gases can pass through port 35.

If the mask is intentionally or inadvertently removed from the patient's face, spring 40 will return the valve 36 to a closed position against the port 35.

As an alternative to using a spring to maintain the valve 36 against the port 35 when the seal 32 is in an expanded state, the valve 36 could be engaged in a track on the seal 32, which would allow the rolling mechanism 42 to slide along the seal 32 within the track. The seal material would be sufficiently resilient to return to its original shape after being worn by the patient, thereby returning the valve to its closed state. In another alternative embodiment, the spring 40 could be attached to the rolling mechanism 42 (or other location along valve segment 36a or 36b) to return the valve to its closed state when the mask was not being worn by a patient or held against the patient's face.

In order that medical personnel can monitor the state of the mask 30, it may be desirable to provide a visual indication of the state of the mask 30. In the embodiment of FIGS. 2a–d, this could be provided coloring the hinge 38, such that a first color is visible through the face plate 34 (for example, by using a clear plastic in the portion of face plate 34 immediately above hinge 38) when the hinge 38 is associated with a closed state, and a second color is visible through the face plate 34 when the hinge 38 is rotated to an open state. Alternatively (or in conjunction with the window and colored hinge 38), the face plate 30 can be partially or wholly formed of a clear plastic material to allow medical personnel to view the state of valve 36. In another embodiment, the position of the valve 36, hinge 38 or spring 40 could be used to enable or disable an electronic circuit which provide a visual indication of the mask through a LED (light emitting diode) or other electronic device.

Further, the hinge could be coupled to a exterior knob or button, such that medical personnel could manually enable or disable the valve.

The advantages of a mask which has a port which automatically maintains an open or closed state response to whether the mask is being worn by a patient or held against the patient's face are significant. First, gases are not inadvertently leaked into the atmosphere, where they can cause significant damage to the health of other patients and medical personnel. Secondly, since gases are only available when the mask is sealed to the patient's face, the medical personnel can be sure that the patient is receiving the proper dosage of gas, without mixing with air from the outside of the mask. Thirdly, expensive gases are not wasted by leakage into the atmosphere.

Figure 3A:
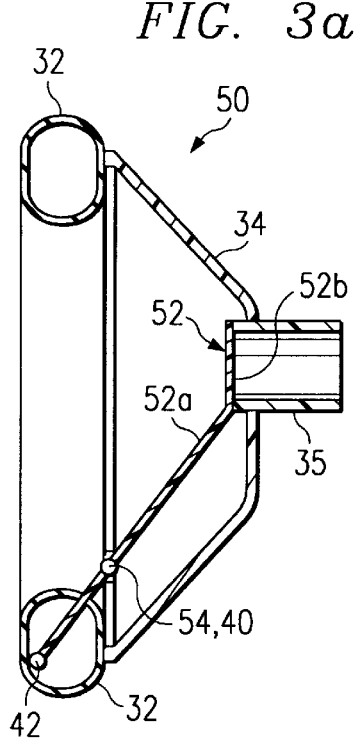
FIGS. 3a, 3b, 3c and 3d illustrate cross sectional side and front views of a second embodiment of a gas delivery mask which controls gas flow through a port responsive to a positive seal between the mask and the patient.
Figure 3B:
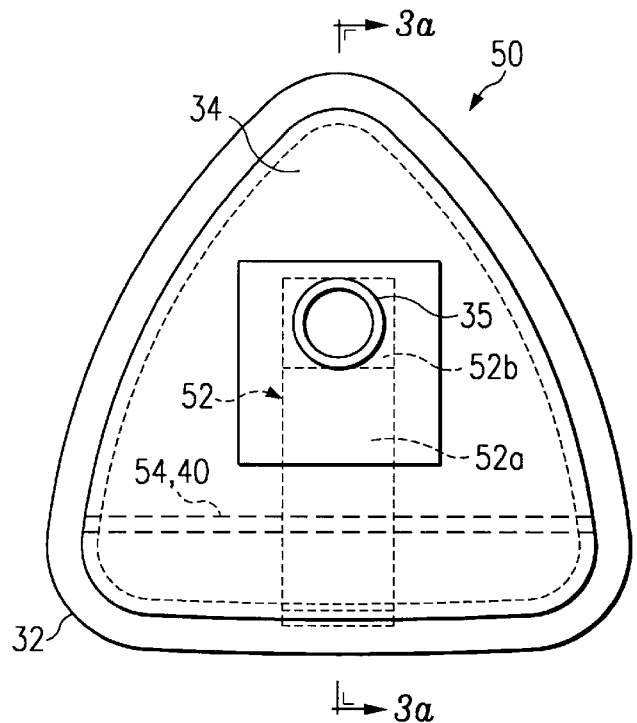
Figure 3C:
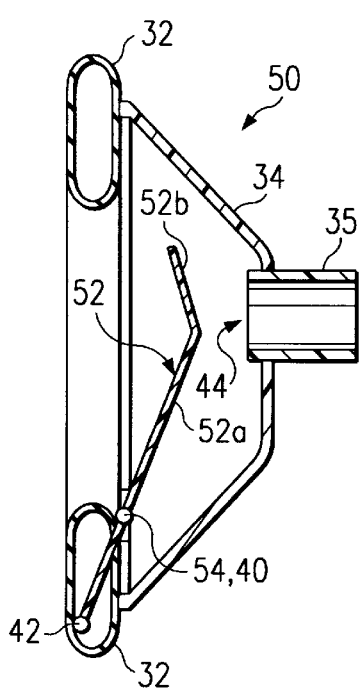
Figure 3D:
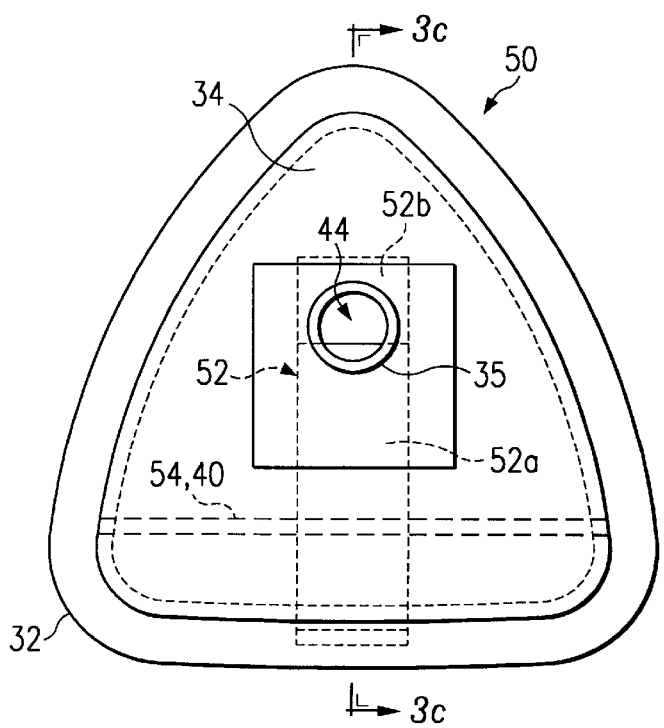

FIGS. 3a–d illustrate a second embodiment of a mask 50. FIGS. 3a and 3b are side cross sectional and front illustrations, respectively, of the second embodiment in a closed state. FIGS. 3c and 3d are side cross sectional and front illustrations, respectively, of the second embodiment in an open state. In this embodiment, reference numbers from FIGS. 2a–d are repeated for clarity. The valve, generally referred to by numeral 52, has a first segment 52a and a second segment 52b in fixed relation to one another; however, unlike the mask 30 of FIGS. 2a–d, valve 52 rotates around a pivot member 54 on segment 52a. Pivot member 54 can be spring loaded to maintain valve 52 in a normally closed position. Alternatively, segment 52a could be guided within tracks formed on the interior of seal 32, such that when seal 32 was in an expanded state, valve 52 would be in a closed position relative to port 35 and when seal 32 was in a compressed state, segment 52a would move in the track to a new position such that valve 52 would be in an open position relative to port 35.

In operation, the mask 50 of FIGS. 3a–d works essentially the same as the mask of FIGS. 2a–d. When the mask is not in contact with a patient's face, the seal 32 is in an expanded state, as shown in FIGS. 3a and 3b. The spring 40 rotates valve segments 52a–b such that segment 52b closes the port 35. Accordingly, in this state, any gases in breathing circuit 18 do not pass through port 35 into the atmosphere. In FIGS. 3c and 3d, pressure from the patients face compresses the seal 32 (or directly presses valve segment 52a), forcing segment 52a to rotate around pivot member 54. As segment 52a rotates, segment 52b, which is held at a fixed angle to segment 36a, rotates away from port 35, resulting in an opening 44 through which gases can pass through port 35. In this state, the patient can breathe gases from the breathing circuit 18 and exhale gases into the breathing circuit 18.

Figure 4A:
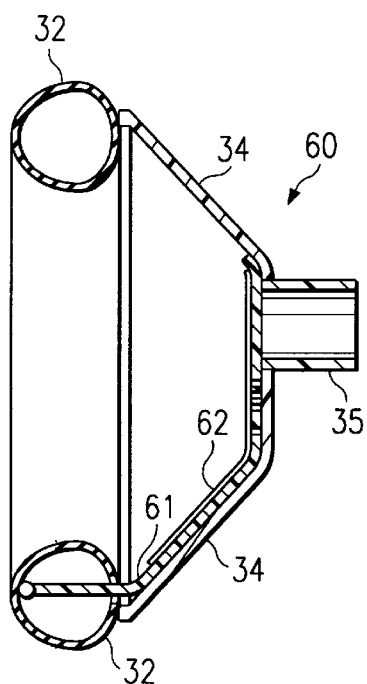
FIGS. 4a, 4b, 4c and 4d illustrate cross sectional side and front views of a third embodiment of a gas delivery mask which controls gas flow through a port responsive to a positive seal between the mask and the patient.
Figure 4B:
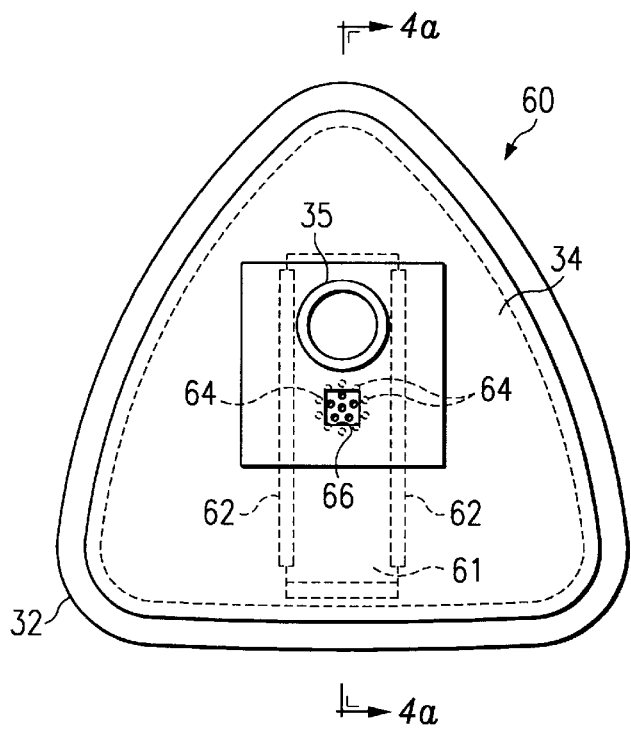
Figure 4C:
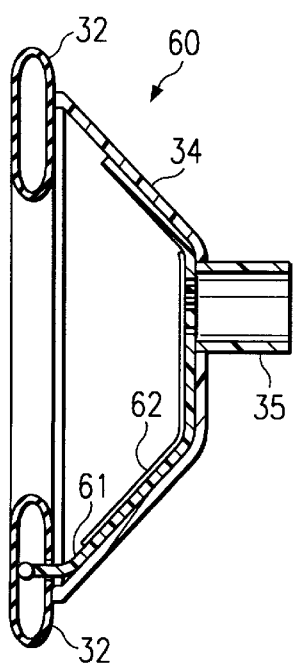
Figure 4D:
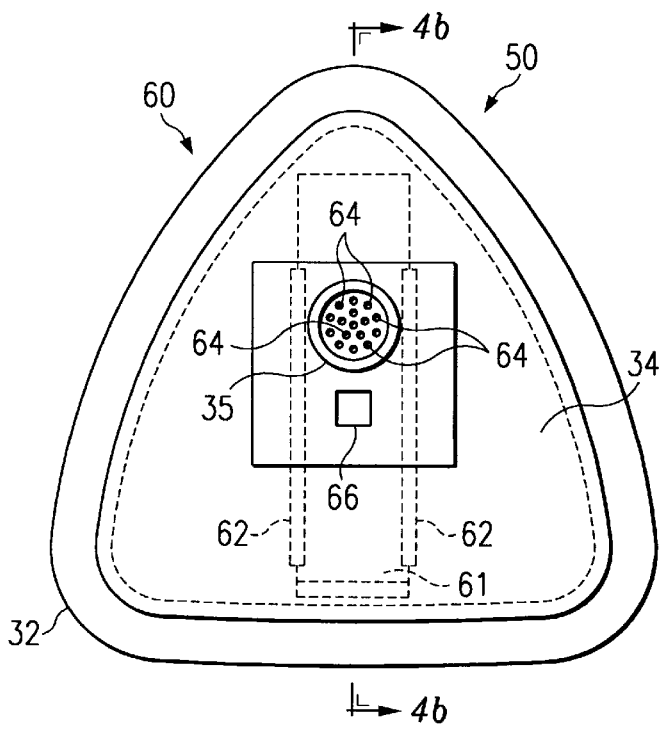

FIGS. 4a–d illustrate third embodiment of a mask using a different type of valve mechanism for providing an opening to port 35 responsive to whether the mask is in contact with the patient's face. FIGS. 4a and 4b are side cross sectional and front illustrations, respectively, of the third embodiment in a closed state. FIGS. 4c and 4d are side cross sectional and front illustrations, respectively, of the third embodiment in an open state. Once again, reference numerals for like parts of the mask are repeated from FIGS. 2a–d.

In this mask 60, the valve comprises a flexible tape 61 which is disposed through guides 62 in the face plate 34. The bottom of the tape is attached to the seal 32. An opening 64 is formed by one or more holes through the tape 61, such that the opening 64 is aligned with port 35 when the mask is being worn and is outside of the port 35 when the mask is not being worn by the patient, or held against the patient's face.

As shown in FIGS. 4a and 4b, when the seal 32 is in an expanded state (when the mask 60 is not being worn), the portion of tape 61 containing the opening 64 is positioned outside of the port 35. A solid portion of tape 61 thus blocks the port 35, inhibiting any gases from passing through the port 35. As the seal 32 is compressed when worn on the patient's face (or directly pushed by the patient's face), as shown in FIGS. 4c–d, the tape 61 is pushed along guides 62, aligning the opening 64 with the port 35. Accordingly, gases may flow through the port 35. Once the mask is removed, the seal reverts to its expanded state, pulling the tape 61 through guides 62, such that the port 35 is once again blocked.

As before, the tape could be marked in different colors which would be visible through a window 66 in the mask, such that medical personnel could see whether the mask was in an open or closed state.

The embodiments shown above illustrate a few of the many ways that a port to a mask could be enabled or disabled responsive to whether the mask was being worn by a patient.

Figure 5A:
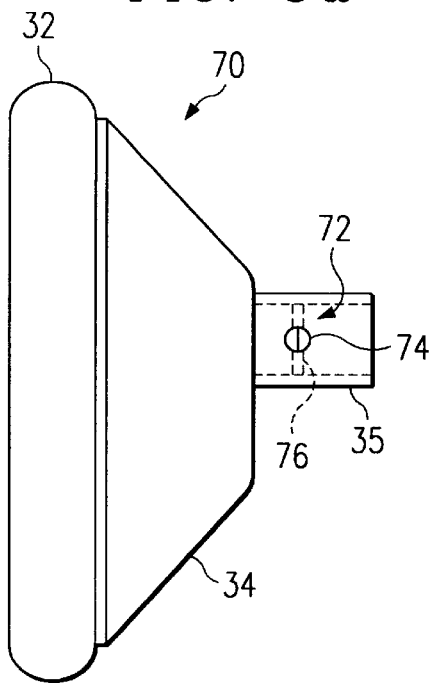
FIGS. 5a and 5b illustrate side views, in closed and open postions, respectively, of a first embodiment of a mask with an integrated manual shut-off valve.
Figure 5B:
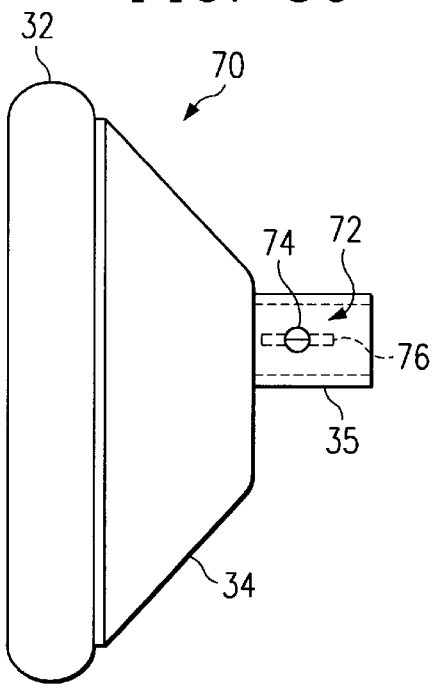

FIGS. 5a and 5b illustrate side cross-sectional and front views, respectively, of an embodiment of a mask 70 with a manual valve 72 which controls flow of gases into and out of the mask. In this embodiment, the valve 72 comprises a knob 74 which protrudes through the port 35. Knob 74 is coupled to disk 76, which has a conforming shape to the interior of port 35. While in the position shown in FIG. 5a, disk 76 blocks the opening through port 35, preventing the flow of gases to or from the patient. In FIG. 5b, with the knob rotated ninety degrees from the position shown in FIG. 5a, the disk 76 provides an opening through port 35.

This embodiment of the invention, which provides a manually configurable valve integrated with the mask, allows medical personnel to easily stop the flow of gases in the vicinity of the patient, without requiring the personnel to stop the flow of gases at the gas source, which may be located several feet from the patient. Accordingly, the mask may be removed quickly from the patient, without exposing personnel to potentially dangerous gases.

Figure 6A:
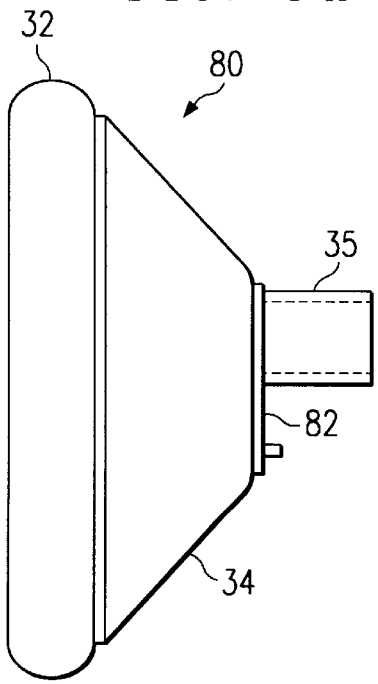
FIGS. 6a and 6b illustrate side and front views of a second embodiment of a mask with an integrated manual shut-off valve.
Figure 6B:
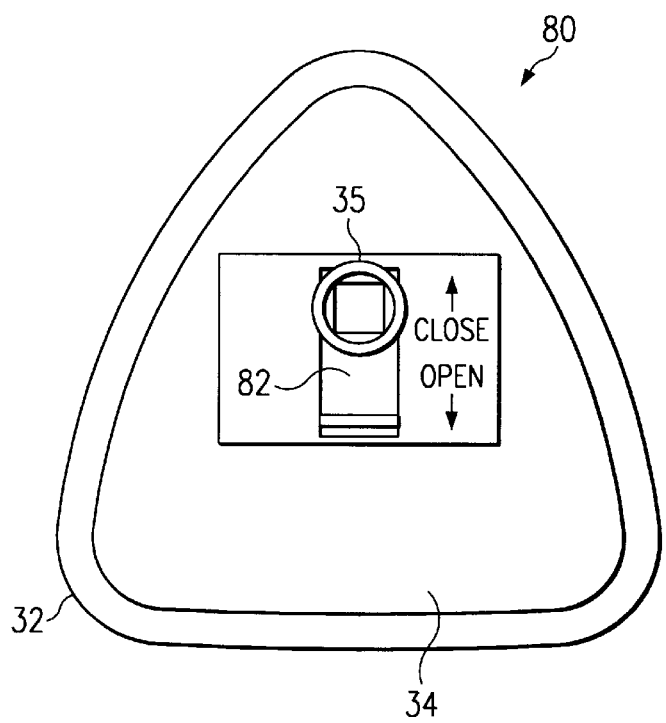

FIGS. 6a and 6b illustrate a second embodiment of a mask with a manual shut off valve. The mask 80 includes a sliding member 82 which is used by medical personnel to enable or disable gas flow through port 35. When the sliding member 82 is pushed away from the port 35, gases may flow through the port 35. When the sliding member 82 is pushed into the port 35, the opening the port 35 is blocked, disabling gas flow therethrough.

This embodiment also provides the advantages discussed in connection with FIGS. 5a and 5b, described above.

Figure 1:
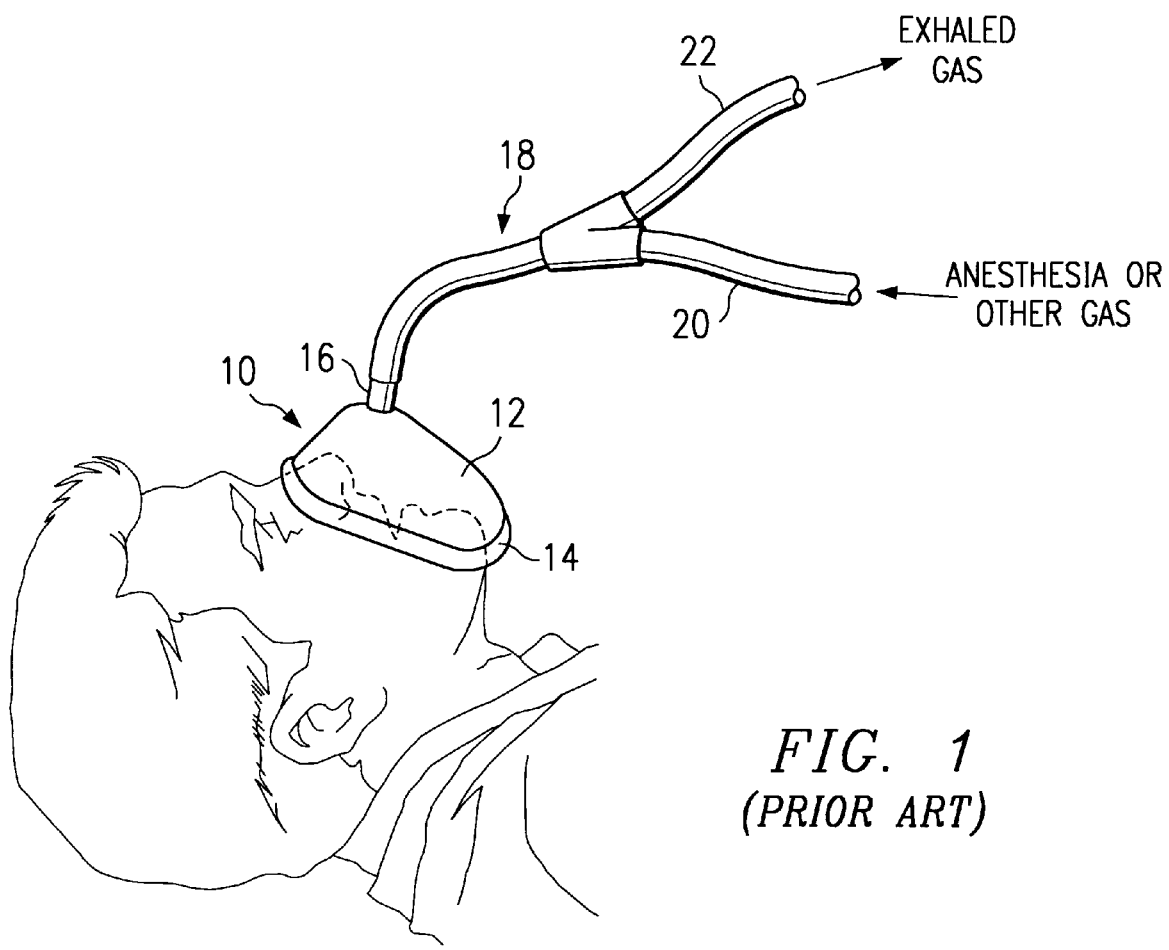
FIG. 1 illustrates a prior art gas delivery mask and breathing circuit.
Figure 7:
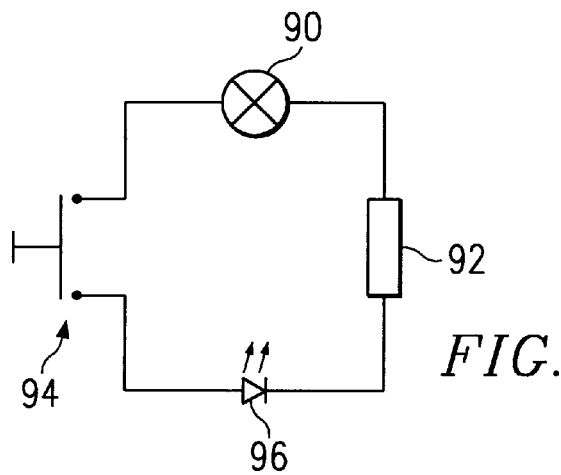
FIG. 7 illustrates an embodiment of the mask using a electronically controlled valve.

FIG. 7 illustrates a schematic representation of an electronic circuit which could be incorporated into a mask to electronically restrict or allow the passage of gas through a mask. A normally closed valve 90 is disposed in port 35. The normally closed valve 90 is selective coupled to a voltage source 92 through switch 94. In the preferred embodiment, an LED (light emitting diode) 96 is located on the exterior surface of the face plate 34 and is coupled to the circuit including the valve 90, switch 94 and voltage source 92.

In operation, when no voltage is applied to the normally closed valve 90, the valve is closed and does not allow gas to pass through the port. When the switch is enabled to complete the circuit, voltage is applied to the valve 90, thereby opening the valve 90 to allow gas to pass through the port 35. The switch is enabled when the patient is wearing the mask. The switch could be a mechanical type, similar to the devices shown above, such that application of the mask to the patient's face pushes a conductive material across two terminals to complete the circuit. Alternatively, the switch could be pressure activated such that a loss of pressure within the interior of the mask would cause the switch to be in a disabled state.

The voltage source could be a small battery embedded in the mask. Since the masks would normally be disposable, the battery could be relatively small, with a relatively short life. Alternatively, the connection to the gas source could carry a small electrical current as well, such that the connection to the voltage source was made when the mask was connected to the breathing circuit.

In all of the embodiments shown above, masks designed for children could have shapes which will not cause apprehension, especially in situations which are likely to be stressful. For example, the mask could be shaped as a plaything, such as an animal shape or a clown shape, which the young patient would enjoy putting on his or her face.

Although the Detailed Description of the invention has been directed to certain exemplary embodiments, various modifications of these embodiments, as well as alternative embodiments, will be suggested to those skilled in the art. The invention encompasses any modifications or alternative embodiments that fall within the scope of the claims.

What is claimed is:

1. A mask comprising:
   a face plate having a port disposed therein for coupling to a gas source;
   a seal surrounding said face plate for contacting a user's face during use of the mask; and
   a valve coupled to said port, said valve switchable between an open position to allow passage of a gas through said port and a closed position to restrict flow of a gas through said port, said valve having an extended member which places said valve in said open position when the user's face pushes the extended member to a first position while the seal is pressed against the user's face and places said valve in said closed position when the user's face is not pressed against the seal.

2. The mask of claim 1 wherein said port couples to a breathing circuit.

3. The mask of claim 1 and further comprising an indicator coupled to said valve for indicating whether the valve is in an open position or a closed position.

4. The mask of claim 1 wherein said valve comprises a pivoting member coupled to said seal such that the pivoting member pivots away from said port when the extended member is pushed by the user's face and pivots against said port when said seal is removed from the user's face.

5. The mask of claim 4 wherein said valve further comprises a spring coupled to said pivoting member to maintain said pivoting member in a closed state when said seal is removed from the user's face.

6. The mask of claim 1 wherein said extended member comprises a sliding member coupled to said seal such that the sliding member slides to a first position which provides communication through said port when said seal is pressed against the user's face and slides to a second position which closes said port when said seal is removed from the user's face.

7. The mask of claim 1 wherein said valve is electronically controlled.

8. The mask of claim 7 wherein said valve is selectively coupled to a voltage source responsive to a switch coupled to the extended member, where the switch is enabled when the patient's face pushes said extended member to said first position.

9. A mask comprising:
- a face plate having a port disposed therein for coupling to a gas source and a seal which changes shape when in contact with a patient;
- a valve, coupled between said seal and said port, having an open position to allow passage of a gas through said port and a closed position to restrict flow of said gas, wherein said valve is automatically switched responsive to whether the patient is in contact with the mask.

10. The mask of claim 9 wherein said valve is in an closed state when said seal is in a decompressed state and said valve is in a open state when said seal is in a compressed state.

11. The mask of claim 9 wherein said valve is electronically controlled.

12. The mask of claim 9 wherein said face plate has a shape of a plaything.

13. A method of providing gas to a patient, comprising the steps of:
- providing a gas source;
- providing a mask with a port for receiving gas from said gas source, said mask having an integral valve for selectively enabling the gas from flowing through the port when in an open position and disabling the gas from flowing through the port when in a closed position, said valve having an extended member which places said valve in said open position when the user's face pushes the extended member to a first position while the seal is pressed against the user's face and places said valve in said closed position when the user's face is not pressed against the seal;
- applying the gas to the port in a mask; and
- placing the mask on the patient such that the extended member is pushed to said first position.

* * * * *